United States Patent [19]

Yutaka et al.

[11] Patent Number: 5,006,828
[45] Date of Patent: Apr. 9, 1991

[54] EXHAUST GAS SENSOR AND PROCESS FOR PRODUCING SAME

[75] Inventors: Yoshida Yutaka; Onaga Kazuo, both of Osaka; Hanada Mariko, Nara; Komatsu Kazunari, Hiroshima, all of Japan

[73] Assignees: Figaro Engineering, Inc.; Mazda Motor Corporation, both of Osaka, Japan

[21] Appl. No.: 376,044

[22] Filed: Jul. 6, 1989

[30] Foreign Application Priority Data

Jul. 14, 1988 [JP] Japan .................. 63-175589

[51] Int. Cl.$^5$ .............................................. H01C 7/00
[52] U.S. Cl. ..................................................... 338/34
[58] Field of Search ............... 338/34, 35; 73/863, 73/27 R

[56] References Cited

U.S. PATENT DOCUMENTS 4,658,632 4/1987 Sasaki ........................ 338/34 X
4,701,739 10/1987 Sasaki et al. ...................... 338/34
4,816,800 3/1989 Onaga et al. ...................... 338/34

FOREIGN PATENT DOCUMENTS 57-74646 5/1982 Japan .

Primary Examiner—Bruce A. Reynolds
Assistant Examiner—Marvin M. Lateef
Attorney, Agent, or Firm—Kerkam, Stowell, Kondracki & Clarke

[57] ABSTRACT

A $BaSnO_3$ exhaust gas sensor and a process for producing the same. Surface reformation of sensor electrodes is done for preventing the deterioration of the sensor response and the corrosion of the electrodes by the Sn in the $BaSnO_3$. After depositing an oxide film such as $La_2Ti_2O_7$ or MgO on the surface of the electrodes, the electrodes are embedded in $BaSnO_3$, and the $BaSnO_3$ is sintered. Through the sintering process, the film of $La_2Ti_2O_7$ or MgO is converted to a conductive complex oxide film by reacting with $BaSnO_3$. The resultant film contains Ba and Sn elements. $CaSnO_3$ and $SrSnO_3$, which are homologous compounds of $BaSnO_3$, are usable in place of $BaSnO_3$.

4 Claims, 12 Drawing Sheets

Fig. 7

EXHAUST GAS SENSOR AND PROCESS FOR PRODUCING SAME

FIELD OF THE INVENTION

The present invention relates to an exhaust gas sensor utilizing a metal oxide semiconductor such as $BaSnO_3$, $SrSnO_3$, $CaSnO_3$, and/or to a process for producing the same. More particularly this invention relates to prevention of the deterioration of the response characteristics of the sensor, and to prevention of the solid phase reaction between the sensor electrodes and the metal oxide semiconductor.

PRIOR ART

The present inventors et al. have been doing close investigations about $BaSnO_3$ exhaust gas sensor. The following is the main cases of the preceding applications.

U.S. Pat. No. 4,701,739,
European Pat. No. 157,328,
U.S. Pat. No. 4,816,800,
U.S. patent application Ser. No. 101,762,
European patent application No. 87 114147.9,
U.S. patent application Ser. No. 323,898,
European patent application No. 89 104423.2.

The $BaSnO_3$ exhaust gas sensor is suitable mainly for the control of air/fuel ratio of automobile engines and also suitable for the control of boiler air/fuel ratio, etc. $CaSnO_3$ and $SrSnO_3$ are homologous compounds of $BaSnO_3$.

The response characteristics of exhaust gas sensors are the most important characteristics. Relating to this the prevention of the deterioration of the response characteristics is also important. Generally the response speeds of exhaust gas sensors are slow at low temperatures, and high at high temperatures. In the case of $BaSnO_3$ there is a significant drift of the response characteristics at low temperatures through its use.

Another problem peculiar to exhaust gas sensors utilizing $BaSnO_3$, $SrSnO_3$, or $CaSnO_3$ is the corrosion of noble metal electrodes of the sensors by Sn in $BaSnO_3$, etc. because of the high activity of Sn in $BaSnO_3$, etc. The corrosion proceeds through alloy formation of Sn and the noble metal by the diffusion of Sn from the semiconductor into the electrodes and makes the electrodes weak. To solve this problem the inventors et al. proposed to use $ZrO_2$ deposited Pt in its crystalline grain boundaries as an electrode material (U.S. Pat. No. 4,816,800). The diffusion of Sn through the crystalline grain boundaries of Pt is prevented by the addition of $ZrO_2$ to Pt, and consequently the corrosion of the electrodes is prevented. In spite of this method, however the protection of the electrodes is not complete in extremely severe atmospheres, and there appears the diffusion of Sn into the electrodes in these atmospheres.

In consideration of these factors the prevention of the deterioration of the response characteristics and more complete protection of the electrodes are necessary for putting the exhaust gas sensor to practical use.

SUMMARY OF THE INVENTION

An object of the invention is to preclude the deterioration of response characteristics of an exhaust gas sensor using the perovskite compound $ASnO_3$ as the sensor material.

Another object of the invention is to prevent the weakening of the sensor electrodes by preventing the diffusion of Sn into the electrodes.

A further object of the invention is to provide a fabrication method of an exhaust gas sensor which fulfills the above objects.

According to this invention, a perovskite compound $ASnO_3$ (A represents at least one member selected from the group consisting of Ba, Sr, and Ca) connected to at least a pair of noble metal electrodes is used as the sensor material.

Furthermore the surface of the noble metal electrodes is covered on the contact portion thereof with $ASnO_3$ with an electrically conductive complex oxide film of $ASnO_3$ and an oxide of a base metal that is different from each metal constituent of $ASnO_3$.

By this complex oxide film, the deterioration of the interface between $ASnO_3$ and the noble metal electrodes is prevented and consequently the deterioration of the response characteristics is also prevented.

The electrically conductive complex oxide film formed upon the electrodes prevents the reaction between $ASnO_3$ and the electrodes, or acts as a buffer layer between them, and prevents the corrosion of the electrodes.

The inventors confirmed the formation of the conductive complex oxide film by the following methods. MgO film was formed on Pt electrode wires by thermal decomposition of Mg ethylate. Then an exhaust gas sensor was prepared by press-molding of $BaSnO_3$ powder with these electrodes embedded therein and by sintering. While MgO is insulating, the Pt electrode wire thus prepared serves as an electrode of $BaSnO_3$, and the change in the sensor resistance resulting from this MgO treatment is not noticeable. This phenomenon can not be explained by the formation of MgO film on the electrode surface. The simplest understanding of this phenomenon is that an electrically conductive complex oxide film of MgO and $BaSnO_3$ was formed by the reaction of MgO and $BaSnO_3$ during the sintering process. The product of this reaction is presumably a mixture of MgO and a compound substituting the Ba site of $BaSnO_3$ with Mg partially, or a mixture of $Mg_2SnO_4$ and $BaSnO_3$.

Various species of base metal oxides film were investigated by the inventors except for MgO. In every case the base metal oxide film was formed upon the surface of the Pt electrode wires, then the electrodes were embedded in $BaSnO_3$ powder, and the $BaSnO_3$ was sintered with the electrodes. For all samples the Pt electrode wires with the base metal oxide film treatment served as the sensor electrodes. The sensor resistance was not greatly dependent upon the species of base metal elements, while the degrees of the prevention of the deterioration of the response characteristics and of the prevention of the electrode corrosion changed with species of the base metal elements. Proved that the base metal oxide film was present as a simple metal oxide film as it was initially, the sensor resistance should differ greatly with the species of base metal elements. The fact that the sensor resistance is insensitive to the species of base metal can not be explained by the supposition that the base metal oxide film is present in its initial state.

For investigating the state of the film, an oxide film of La-Ti was formed on the Pt electrodes. The film was identified as $La_2Ti_2O_7$, an insulating material, by X ray diffraction analysis at a portion thereof out of contact with $BaSnO_3$. In spite of the formation of the insulating film, the sensor resistance did not change greatly. It is difficult to explain the fact that the resistance change was not great, based upon the supposition that the La-Ti oxide film was present on the electrode surface simply.

An exhaust gas sensor using this La-Ti oxide film was attached to the exhaust manifold of an automobile engine, and then actually used. An elementary analysis about La, Ba, Sn, Pt of the La-Ti oxide film was done after the use. It revealed that Ba content and Sn content were each 40 atm %, La content was 10 atm %, and Pt content was 10 atm %. The main constituents of the film were Ba and Sn derived from the surrounding $BaSnO_3$. Ba/La and Sn/La ratios were 4. While the initial thickness of this film was 1 $\mu m$, it swelled to 2 $\mu m$ after the use. This indicates that the film absorbed Ba and Sn from $BaSnO_3$ through the use. Considering that the film thickness was doubled with the use, the initial values of Ba/La and Sn/La were presumed approximately 2. This indicates that the film contained Ba and Sn from the first. Both the resistance drift and the response speed drift of this sensor were slight despite the actual use. This fact suggests that the film changed continuously from the initial state to the final state and there were no essential changes between them. So it is improper to consider that the initial film had been a metal oxide film of La and Ti only and that then it changed to a complex oxide film of La, Ti, Ba, and Sn.

These results are summarized to a conclusion. Base metal oxide films were formed on the surface of the Pt electrodes, then the electrodes were embedded in $BaSnO_3$, and $BaSnO_3$ was sintered. $BaSnO_3$, like $SrSnO_3$ and $CaSnO_3$, easily reacts with various base metal oxides in solid phase. For example by the reaction with MgO, $Mg_2SnO_4$ is produced. The Ba site of $BaSnO_3$ may be substituted with La, Mg, Sr, Ca, etc. The Sn site of $BaSnO_3$ may be substituted with a transition metal element such as Ti. Most of the compounds thus produced are electrically conductive. So it is evident that the base metal oxide films react with $BaSnO_3$ through the sintering process and complex oxide films between them are formed. When considering thus, the fact that insulating base metal oxide films are usable and the results of elementary analysis of La-Ti film may be explained. The fact that the sensor resistances are insensitive to the species of base metal oxides is also easily explainable.

The oxide film thus formed reforms the interface between $ASnO_3$ and the electrodes and consequently prevents the deterioration of the response characteristics. The film also pevents the Sn diffusion into the electrodes by lying between them. The film gradually absorbs the surrounding $BaSnO_3$ with use.

According to experiments of the inventors, particularly preferable base metal oxides are oxide of La and Ti, oxides of Fe and alkaline earth elements that are different from the alkaline earth element in $ASnO_3$, and oxides of alkaline earth elements that are different from the alkaline earth element in $ASnO_3$. Also usable are a simple La oxide, oxide of La and Co, oxide of La and Ni, oxide of La and Cu, etc. Furthermore oxide of Fe and Co is usable.

When using $BaSnO_3$, more preferable materials are oxide of La and Ti, oxide of Sr and Fe, and magnesium oxide.

Among these films the oxide film of La-Ti is most uniform and complete. Probably relating to this, the protection of the electrodes against the corrosion is most complete when the La-Ti oxide film is used. Except for the La-Ti film, the films were found to have many pores and deposited on the surface of the electrodes in the form of clusters, when observed before embedding in $BaSnO_3$.

The thickness of these films increases gradually with their use. In embodiments the films whose initial thickness were about 1 $\mu m$ when produced were used, and the preferable range of initial thicknesses of the film is 0.01 to 3 $\mu m$.

The following is an example of production method of the exhaust gas sensor. A base metal oxide film is first formed upon the surface of noble metal electrode wires etc. Then these electrodes are emebedded in $BaSnO_3$ powder, and the $BaSnO_3$ is press-molded and sintered. Through the sintering the base metal oxide reacts with $BaSnO_3$ into a conductive complex oxide film.

The shape and structure of the sensor are arbitrary. For example a sensor using noble metal film electrodes with the conductive complex oxide film coating and $ASnO_3$ covering the electrodes is usable. While Pt-$ZrO_2$ electrodes are used in the embodiments, Ir, Rh, Pt-Rh, simple Pt, etc. may be usable as electrode materials.

BRIEF DESCRIPTION OF THE DRAWINGS

FIG. 1 shows variations in dynamic resistances and in static resistances;

FIG. 2 shows variations in response speeds;

FIG. 3 to FIG. 4(F) show variations in the response patterns of exhaust gas sensors;

FIG. 3 shows the results obtained by a conventional sensor;

FIG. 4(A) shows the results obtained by the sensor with a complex oxide film of La-Ti oxide and $BaSnO_3$ on the electrodes;

FIG. 4(B) shows the results obtained by the sensor with a complex oxide film of La-Cu oxide and $BaSnO_3$ on the electrodes;

FIG. 4(C) shows the results obtained by the sensor with a complex oxide film of Mg oxide and $BaSnO_3$ on the electrodes;

FIG. 4(D) shows the results obtained by the sensor with a complex oxide film of Sr-Fe oxide and $BaSnO_3$ on the electrodes;

FIG.4(E) shows the results obtained by the sensor with a complex oxide film of La-Cr oxide and $BaSnO_3$ on the electrodes;

FIG. 4(F) shows the results obtained by the sensor with a complex oxide film of Ni oxide and $BaSnO_3$ on the electrodes;

FIG. 5 shows variations in dynamic resistances;

FIG. 6 shows variations in static resistances;

FIG. 8 shows the result obtained with an conventional electrode un-coated by an oxide film;

FIG. 9 shows the results obtained with an electrode coated by a complex oxide film of La-Ti oxide and $BaSnO_3$;

FIG. 10 shows the results obtained with an electrode coated by a complex oxide film of La oxide and $BaSnO_3$;

EMBODIMENT

Structure of Exhaust Gas Sensor

Figure 7:
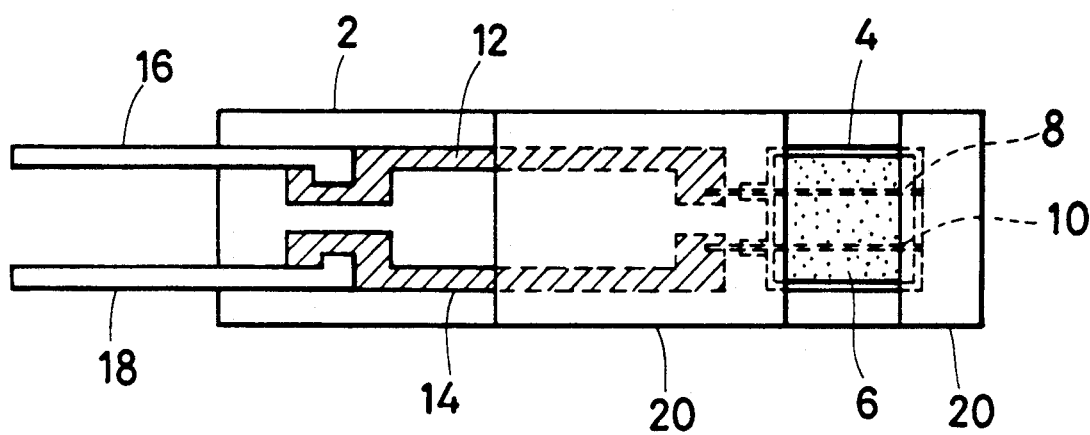
FIG. 7 is a plan view of an exhaust gas sensor of the embodiment.

The structure of an exhaust gas sensor used in experiments is shown in FIG. 7. Indicated 2 is a heat resistant insulating substrate such as $Al_2O_3$, and it has a recess 4 at its top end for accommodating a sintered body 6 of a perovskite metal oxide semiconductor, such as $BaSnO_3$, $SrSnO_3$, or $CaSnO_3$. A pair of noble metal electrodes 8, 10 are embedded in the sintered body 6, and connected to outer leads 16, 18 through Pt film electrodes 12, 14. The surfaces of the electrodes 8, 10 are covered with a complex oxide film of a base metal oxide and $BaSnO_3$ at least at the contact portion thereof with the sintered body 6 of $BaSnO_3$. This film will be described later. Indicated 20 is a compact plasma spray coating for maintaining the sintered body 6 in the recess 4 and for protecting the electrodes 8, 10 from exhaust gases by covering their exposed surfaces. The coating 20 used was a $MgAl_2O_4$ film of 20 μm in thickness and covers about 20% of the surface of the sintered body 6.

Sample Series 1

The sintered body 6 of $BaSnO_3$ was prepared according to the method proposed by the inventors et al. previously (U.S. patent application Ser. No. 101,762 and European patent application No. 87 114147.9). The crystals of $BaSnO_3.7H_2O$ were precipitated by reacting a sodium stannate aqua solution with a barium chloride aqua solution in a strong alkaline medium. Needle-like crystals of $BaSnO_3.3H_2O$ were separated out by recrystallization at elevated temperatures and water washings through intermediate crystals of $BaSnO_3.5H_2O$. $BaSnO_3$ having the needle-like appearance of $BaSnO_3.3H_2O$ was prepared by thermal decomposition at 1200° C. in air.

$ZrO_2$-added Pt wires of 60 μm in diameter (U.S. Pat. No. 4,816,800) were used as the sensor electrodes 8, 10. In these electrodes, about 0.06 wt % $ZrO_2$ is added in their platinum crystalline grain boundaries for preventing the diffusion of Sn through the boundaries.

The electrodes 8, 10 were immersed in an ethanol solution of a base metal ethylate, and the ethylate was thermally decomposed after drying to a base metal oxide film as deposited on the electrode surface. Various species of the base metal oxide films were prepared by the above described method. The concentration of each ethylate in the ethanol solution was 4.5 wt % calculated as its stable oxide. For example, La was calculated as $La_2O_3$, La-Ti as $La_2Ti_2O_7$, La-Co, La-Ni, La-Cu, and Sr-Fe as perovskite compounds such as $LaCoO_3$, $LaNiO_3$, etc. and Fe-Co as $FeCo_2O_4$. The thermal decomposition of the ethylate was carried out by either one of the following two conditions: by decomposition at 800° C. in air (low temperature type), and by two step decomposition first at 800° C. in air and subsequently at 1400° C. in air (high temperature type).

The results obtained by the high temperature type are shown in the following unless otherwise specified.

The electrode surfaces treated at 1400° C. were observed by electron micrography before embedding in $BaSnO_3$. The La-Ti film formed was most uniform. This film was found almost uniform and without pores. The films formed by other materials were found cluster-like and there were observed pores or exposed surface portions of the electrode between the clusters. The cluster like films had wrinkles on their surfaces. The films treated at 800° C. were more uniform than those treated at 1400° C.

The X ray diffraction analysis of the La-Ti oxide film treated at 1400° C. revealed the formation of $La_2Ti_2O_7$. This film is insulating. The diffraction analysis of La-Ni, La-Co, Sr-Fe, and Fe-Co did not reveal the formation of $LaNiO_3$, $LaCoO_3$ $SrFeO_3$, etc. The results of elementary analysis of these materials indicated that the films were nonstoichimetric and some of the constituents were lost by vaporization. The thickness of the films observed before embedding in $BaSnO_3$ was 0.5~1 μm for both 1400° C. treatment and 800° C. treatment.

The needle-like particles of $BaSnO_3$, without pulverization, were filled into a die with a pair of electrodes 8, 10 and press-molded into a chip of 2 mm×2 mm×1 mm thickness under a pressure of 4 tons/cm². Then the sintered body 6 shown in FIG. 7 was prepared by sintering at 1400° C. in air for two hours. Ofcourse the particles of $BaSnO_3$ may be pulverized before the molding. The preferable conditions of the sintering are at 1200~1600° C., for 1~12 hours, and in non-reducible atmospheres such as in air, oxygen, and nitrogen.

During the sintering process, the base metal oxide film on the electrode reacts with $BaSnO_3$ and is converted to a complex oxide film between the base metal oxide and $BaSnO_3$. Generally the resultant complex oxide film is electrically conductive. For example the insulating films of MgO and $La_2Ti_2O_7$ were found to change to conductive films by the reaction with $BaSnO_3$. The products of MgO and $BaSnO_3$ reaction are presumed to be $Mg_2SnO_4$ and some compounds that were formed by the partial substitution of Ba site in $BaSnO_3$ with Mg. In the case of $La_2Ti_2O_7$ the formation of La-Sn compounds and Ba-Ti compounds are expected. Futhermore the substitution of Ba site by La and Sn site by Ti in $BaSnO_3$ is also expected. The surface of the electrodes with the La-Ti film was observed at an inner portion of the $BaSnO_3$ sintered body 6. The initial thickness of the film was about 1 μm.

The base metal oxide film may be formed by sputtering, ion-plating, or thermal decomposition of base metal hydroxide sols other than the above described method. Ofcourse the film thus produced is converted to a conductive film by the reaction with $BaSnO_3$ or the like. The structure of the sensor is arbitrary, for example an exhaust gas sensor utilizing noble metal film electrodes coated with the conductive complex oxide film and further laminated by $BaSnO_3$ or the like may be usable. Other electrode materials such as Rh, Ir, Pt-Rh, Pt-Au, and Rh-Ir, etc. than $Pt-ZrO_2$, are also usable.

Characteristics of exhaust gas sensors are influenced by poisonous components of exhaust gases such as P, Zn, Pb, and Cl, and by highly reducing or highly oxidizing atmospheres at high temparatures. In these factors the influence of highly reducing atmospheres at high temparatures is most significant. As an acceleration test for the deterioration of sensors, they were treated in an atmosphere of eqivalence ratio $\lambda=0.85$ at 900° C. The atmosphere used was an exhaust gas of methane-air combustion ($\lambda=0.85$). The exhaust gas was cooled to adjust its dew point to 60° C. and reheated to 900° C. by an electric furnace.

Figure 1:
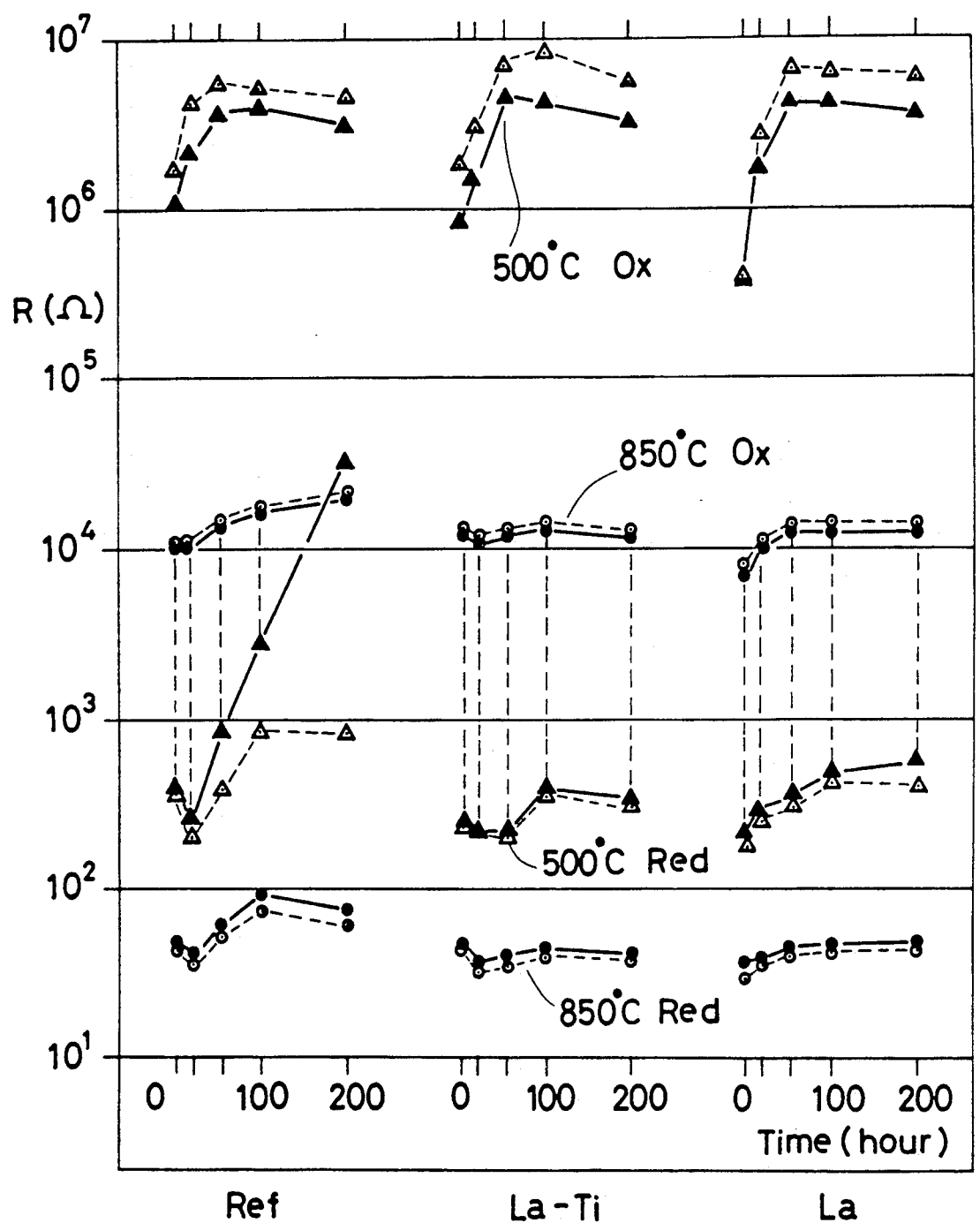
FIG. 1 to FIG. 6 are characteristics diagrams showing the durability of exhaust gas sensors against a reducing atmosphere at a high temparature.

The variations in sensor resistance R after 200-hour treatment are shown in FIG. 1. The symbol "Ref" denotes a comparative example without the complex oxide film on the electrodes. Symbols "La", etc. denote the base metal constituent of the film. The word "La film", etc. means the conductive complex oxide film resultant from the reaction of the La oxide film, etc. and $BaSnO_3$. The species of complex oxide films are designated by the base metal constituent in this specification. The same wordings as above are used in the following description. The data of FIG. 1 are the results of the high temperature type (thermal decomposition of ethylates at 1400° C.) and similar results were obtained by the thermal decomposition at 800° C. The atmospheres used in the measurement were those of $\lambda=0.98$ (Red) and of $\lambda=1.02$ (Ox), and the temparatures of them were 500° C. and 850° C. The symbols ○ and △ denote stationary resistances and ● and ▲ denote dynamic resistances when the atmosphere was changed between Ox and Red every 1 second with a 2-second period. Results shown are Ox resistances at 500° C., Ox resistances at 850° C., Red resistances at 500° C., and Red resistances at 850° C. from upside to downside of the figure. The differences between Red resistances at 500° C. and Ox resistances at 850° C. show the detection signals for air/fuel ratio when the temperature of exhaust gas changes at random between these values. The differences between the static characteristics and dynamic characteristics show the response times for the changes of the atmospheres.

The dynamic resistance of the comparative example drifted by the 200-hour treatment and the Red resistance at 500° C. exceeded the Ox resistance at 850° C. finally. The drift was significant in the Red resistance at low temperatures (500° C.). To the contrary the drifts of the dynamic characteristics in the embodiments were not so significant and the differences between the Ox resistance at 850° C. and the Red resistance at 500° C. remained nearly the same as the initial values.

Figure 2:
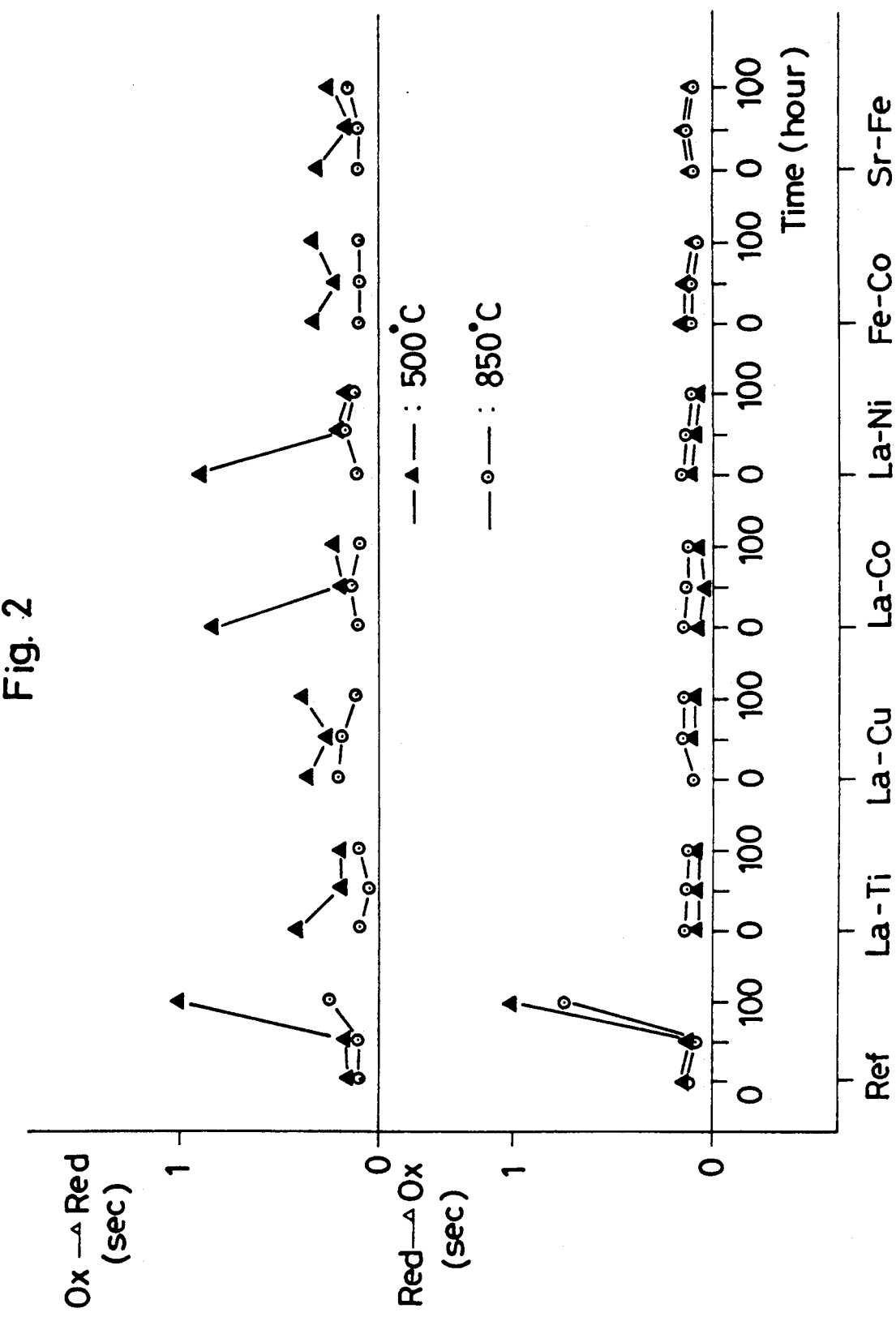

It is evident from FIG. 1 that the deterioration of an exhaust gas sensor is attributable mainly to the decrease of response speed. FIG. 2 shows variations in response time exhibited by other examples similarly treated. The measurement conditions and meansings of the symbols in the figure are the same as in FIG. 1 except that 106-hour treatment was used. The specimens used were those in which the base metal ethylates were decomposed at 1400° C., and similar results were obtained from the specimens decomposed at 800° C. The upper portion of the figure shows the 10%–90% response time from Ox to Red, and the lower portion shows the 10%–90% response time from Red to Ox. While in the comparative example the response speed decreased greatly by the 106 hour treatment, in the embodiments the decreases were small or negliegible. The initial response speeds of La-Co and La-Ni film were low. For example the response times from Ox to Red at 500° C. were almost 1 second. However by this treatment the response speeds of the sensors using these films were improved. So when using these films, some aging before actual use is necessary.

Sample Series 2

Another powder of $BaSnO_3$ was prepared under the same conditions as used for the Sample Series 1. Five kinds of the electrodes, non-coating (comparative example), La-Ti treatment (La-Ti), Mg treatment (Mg), La-Cr treatment (La-Cu), and Sr-Fe treatment (Sr-Fe) were prepared. These electrodes were prepared in exactly the same way as in Sample Series 1. These electrodes were embedded in the $BaSnO_3$ chips and the chips were sintered. Through the sintering of the chips the oxides such as La-Ti oxide, Mg oxide, etc. react with $BaSnO_3$ and were converted to conductive complex oxide films. These processes were done in exactly the same way as in Sample Series 1.

Figure 3:
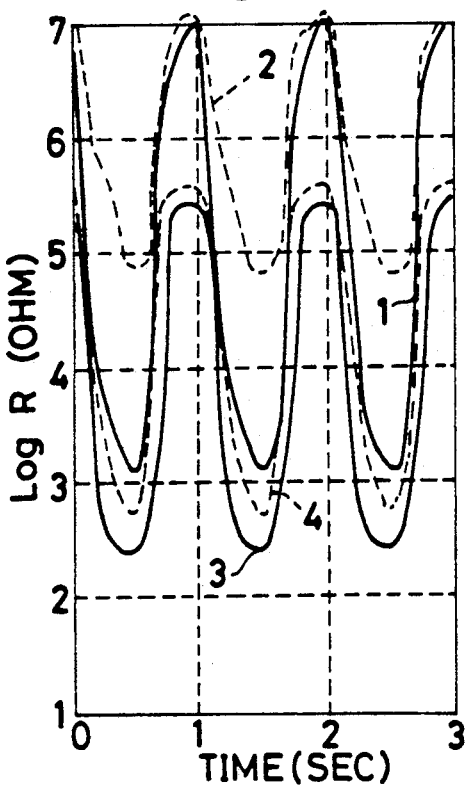

The resultant sensors were treated for 150 hours in an atmosphere of $\lambda=0.85$ (exhaust gas from methane-air combustion) at 900° C. FIG. 3 shows the change in the response pattern of the comparative example by this tratment and FIGS. 4(A)~4(F) show those of embodiments. The solid lines in the figures denote the response patterns before the treatment and the broken lines denote the response patterns after the treatment. The measurement temparatures were 500° C. and 850° C. and the atmospheres used in the measurement were changed between $\lambda=0.98$ and $\lambda=1.02$ every 0.5 second with a period of 1 second. Samples used in this experiment are listed in Table 1.

TABLE 1

Figure 4:
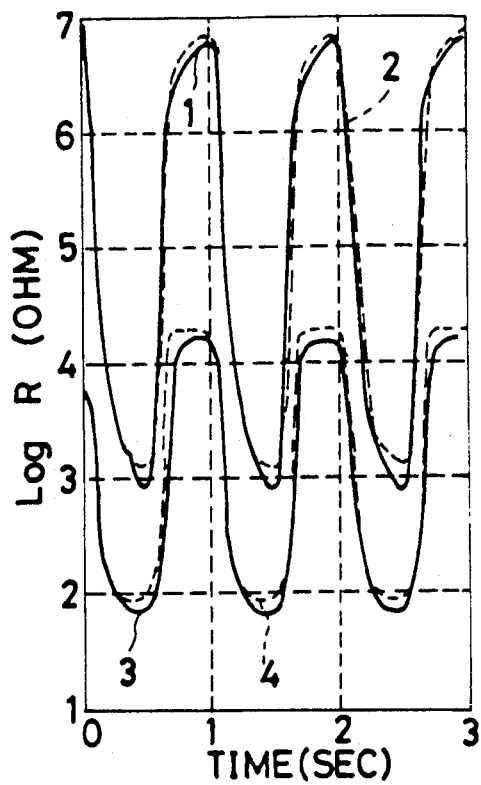
Figure 4:
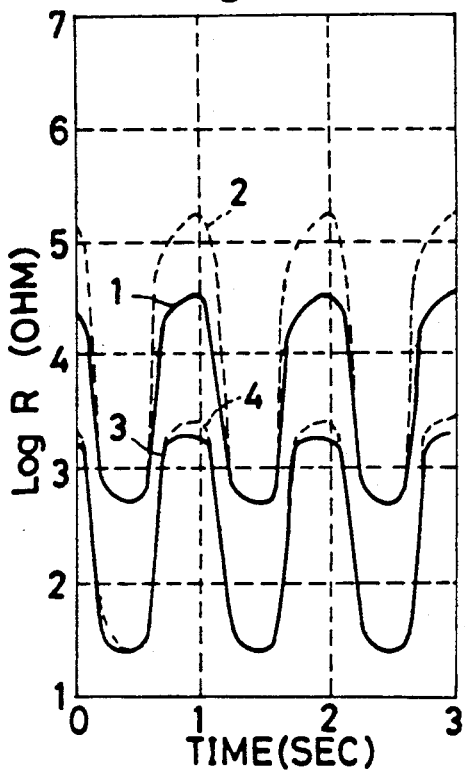
Figure 4:
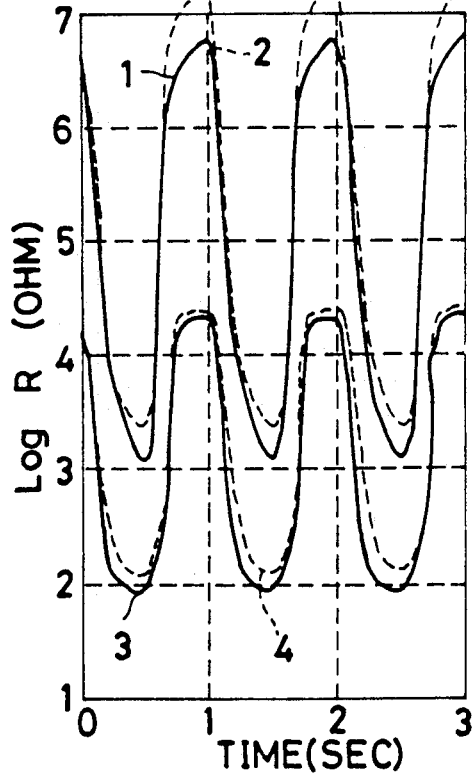
Figure 4:
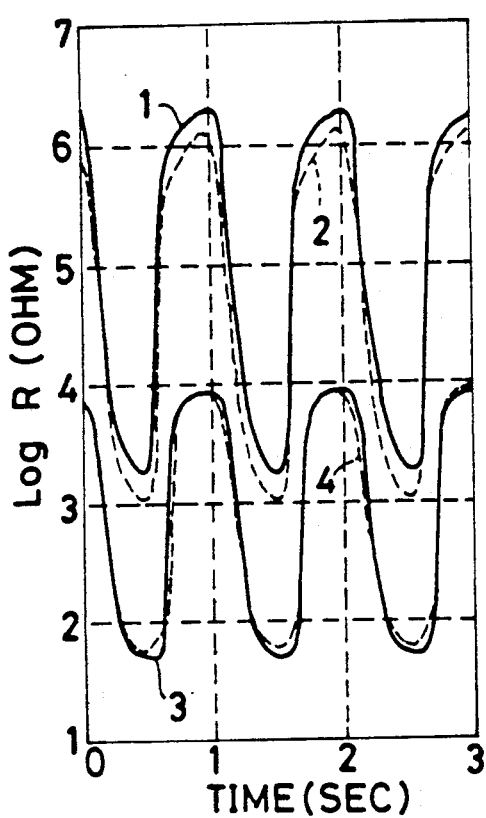
Figure 4:
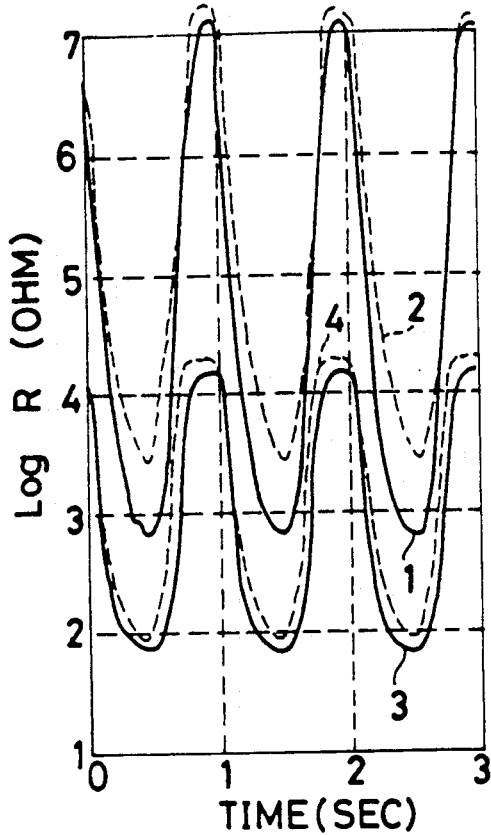
Figure 4:
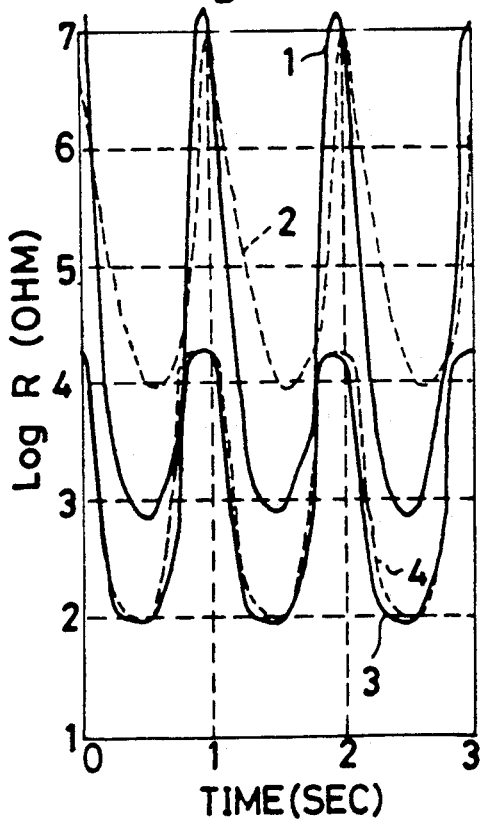

| FIG. 3 and FIG. 4 | |
|---|---|
| FIG. 3 | comparative example |
| FIG. 4(A) | La—Ti film |
| FIG. 4(B) | La—Cu film |
| FIG. 4(C) | Mg film |
| FIG. 4(D) | Sr—Fe film |
| FIG. 4(E) | La—Cr film |
| FIG. 4(F) | Ni film |

In the comparative example the response at 500° C., especially the response to the reducing atmosphere from the oxidizing atmosphere, deteriorated through this test. Among the embodiments La-Ti film, Mg film, and Sr-Fe film show especially desirable results.

Figure 5:
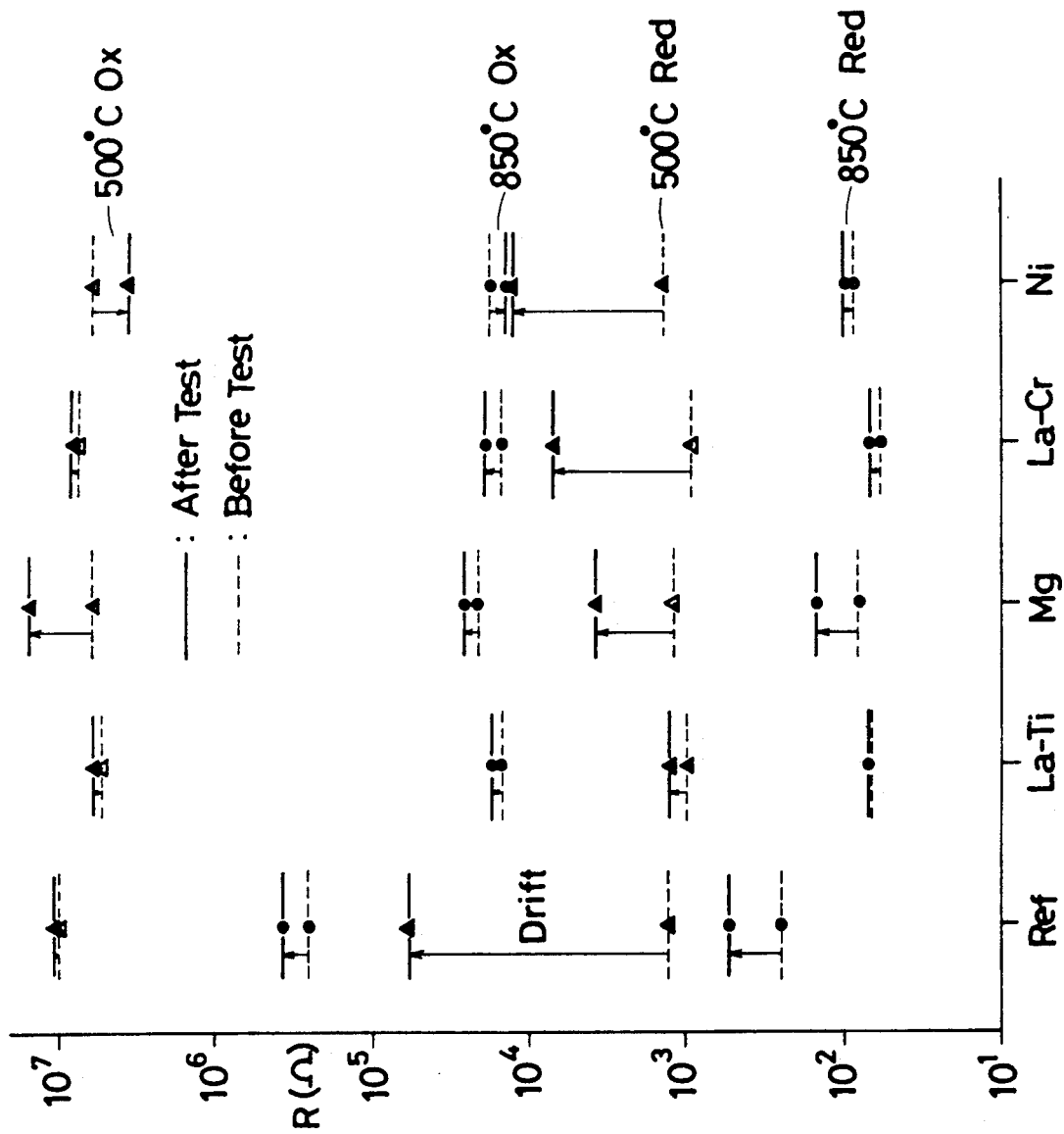

FIG. 5 shows the dynamic resistance changes by the same treatment as those of FIG. 3 and FIGS. 4(A) to (F). In the figure the maximum resistances are denoted by Ox level and the minimum resistances are denoted by Red level, when the atmosphere was changed every 0.5 second between $\lambda=0.98$ and $\lambda=1.02$ with a 1-second period. The solid lines (with solid black symbols) in the figure show the levels after the treatment, and the broken lines (with blank symbols) show those before the treatment. While the results of FIG. 3 and FIGS. 4 are those obtained by one sample of each sensor, the results of Fig. 5 are average values of two samples of each sensor.

The results of FIG. 5 agree qualitatively with the results of FIG. 3 and FIGS. 4 and indicate that the film coating on the electrodes prevents the drift of dynamic resistance and that La-Ti film and Mg film are more preferable than La-Cr film and Ni film.

Figure 6:
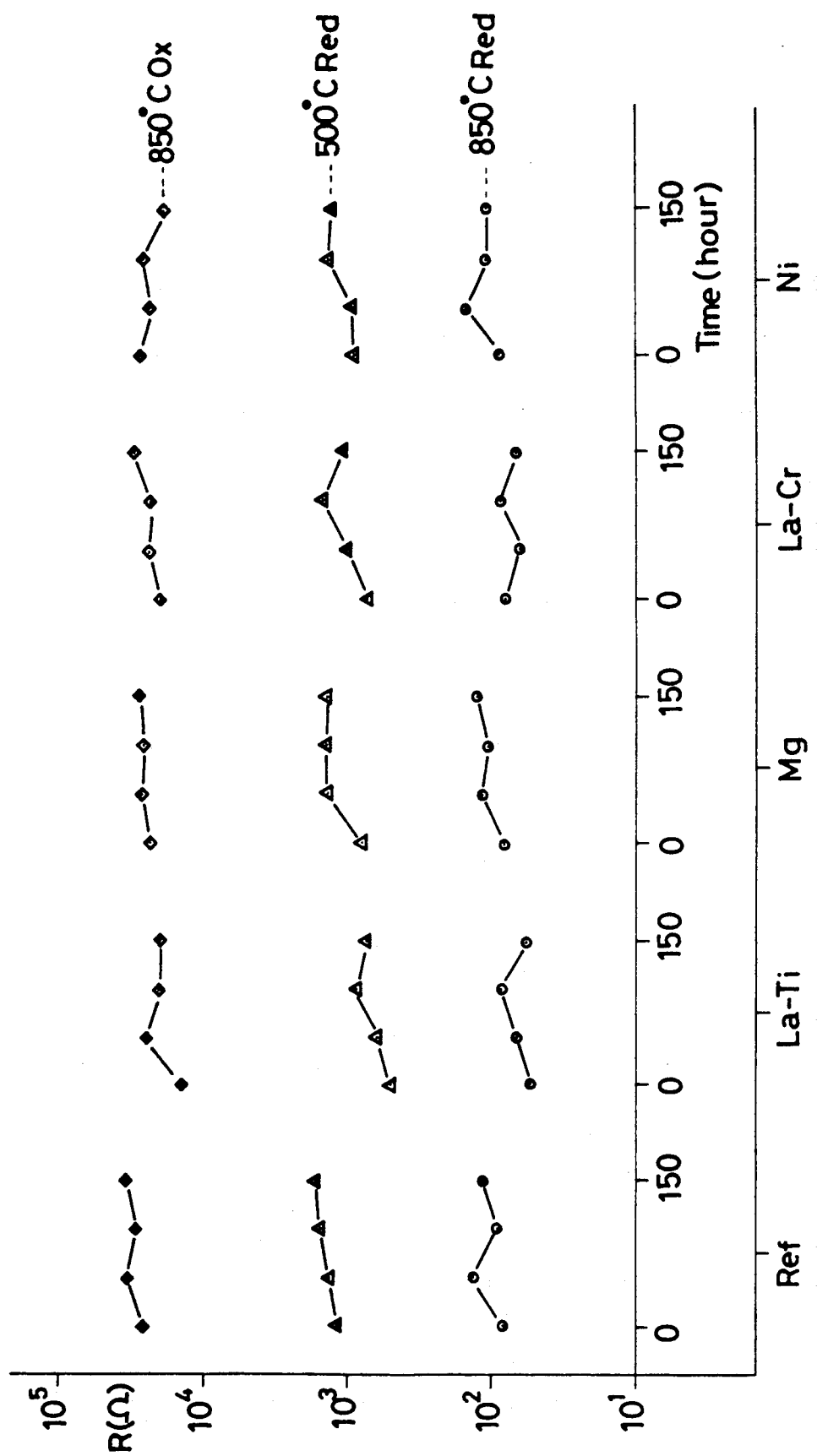

FIG. 6 shows the drift of the stationary resistance by the same treatment as in the case of FIG. 5. The drifts of static characteristics are smaller than those of the dynamic characteristics.

Corrosion of Electrodes

Figure 8:
FIGS. 8 to 10 are elementary analysis photographs showing Sn diffusion into pure Pt electrodes.
Figure 9:
Figure 10:
Figure 11:
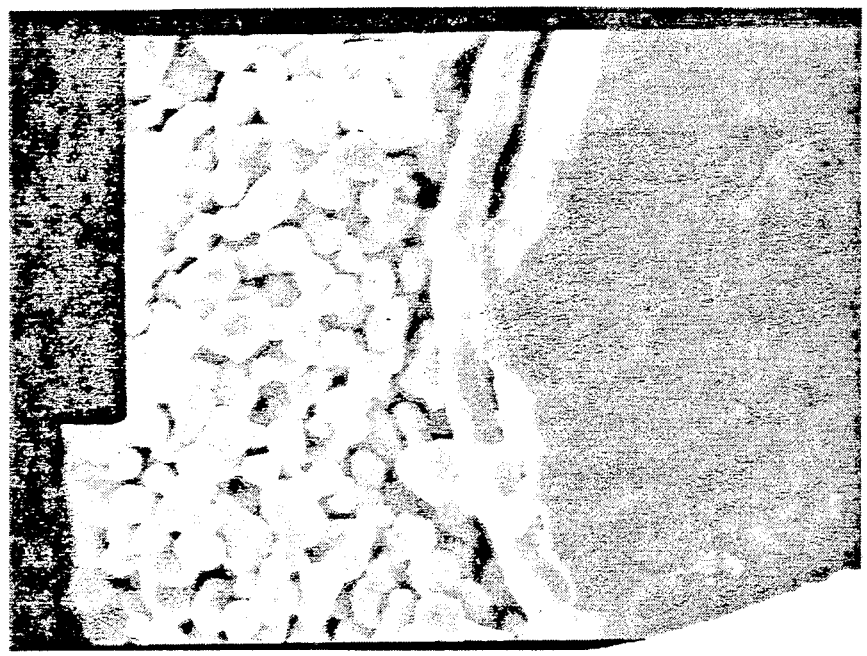
FIG. 11 is an electron photomicrograph at a magnification of ×3,000 showing a complex oxide film of La-Ti oxide and $BaSnO_3$ on a $Pt-ZrO_2$ electrode.

Dissolution of Sn into Pt electrodes was observed in the electrode sections after the treatment in the previously described high-temparature reducing atmosphere for 200 hours using the sensors of sample Series 1 as the experimental samples. Simple Pt wires were used as the material of the electrodes 8, 10 to promote the solution of Sn into the electrodes. More significant diffusion of Sn was observed at the cathodes of the sensors than those at the anodes. Sn distributions in sections are shown in FIG. 8 to FIG. 10. FIG. 8 shows the result of the comparative example, FIG. 9 shows that of La-Ti film, and FIG. 10 shows that of La film. These FIGS. are photographs of cathode electrodes at ×600.

The black portion in the center of FIG. 9 (La-Ti film) shows the electrode that is slightly influenced by Sn diffusion, and the surrounding white portion shows Sn in the $BaSnO_3$. In the case of the La film, the dissolution of Sn was observed in the right upper portion and left under portion of the electrode. Similar results were observed in the embodiments other than the La-Ti film. The result that the La-Ti film is excellent for protecting the electrode against corrosion seems to have some correlation with the fact that the La-Ti film is exceptionally uniform. In the comparative example Sn diffused through the entire section of the electrode except its center and the electrode swelled by alloy formation with Sn.

La-Ti Complex Oxide Film

Figure 12A:
FIG. 12(A) is another electron photomicrograph, ×800, of a complex oxide film of La-Ti oxide and $BaSnO_3$ on a $Pt-ZrO_2$ electrode.
Figure 12B:
FIGS. 12(B) to (D) are elementary analysis photographs of electrodes showing the distributions of La, Pt, and Sn at the same position as in FIG. 12(A) respectively.
Figure 12C:
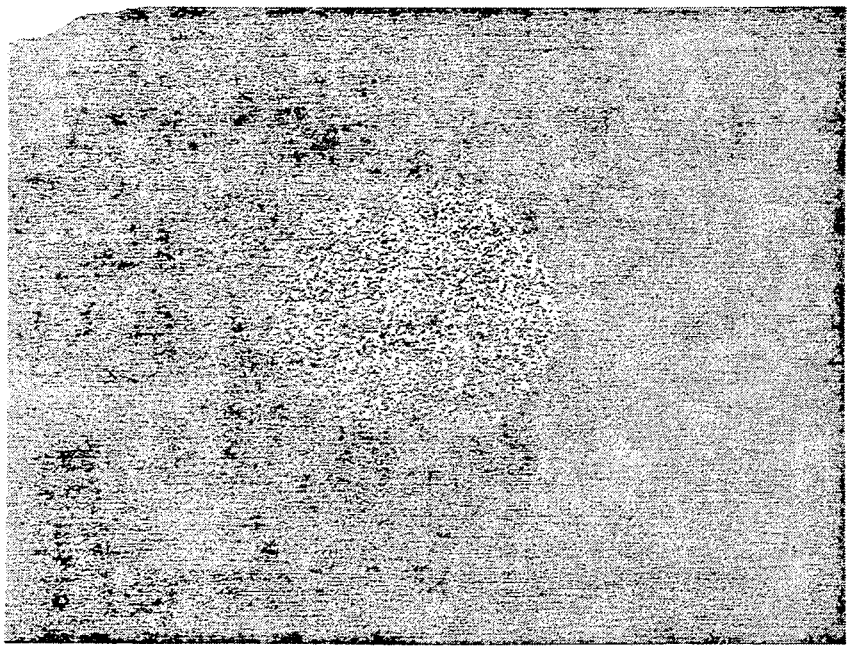
Figure 12D:
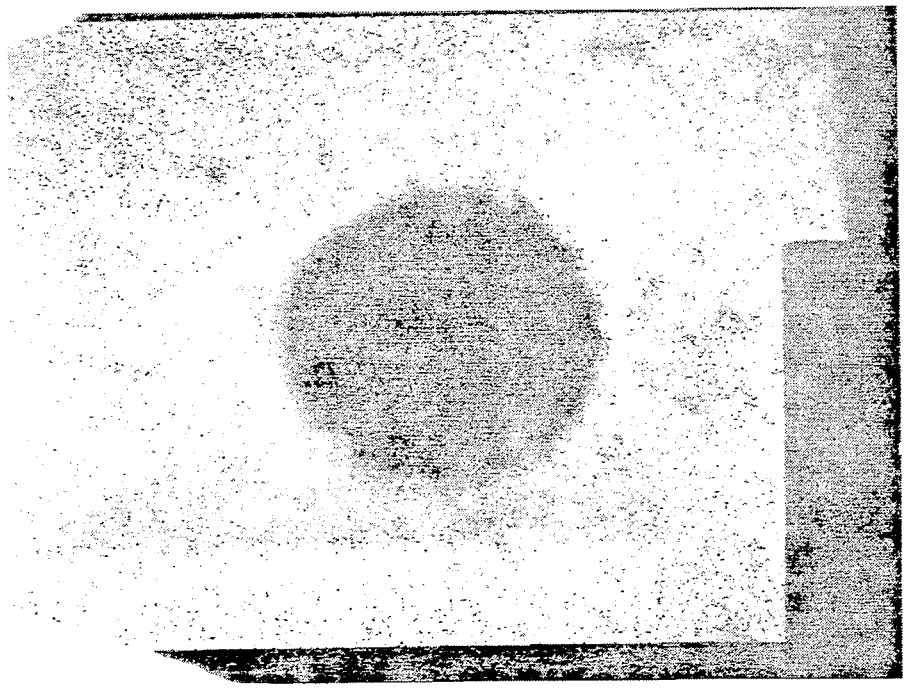

FIG. 11 and FIGS. 12(A) to 12(D) show the La-Ti film and the distributions of La, Sn, and Pt after 50,000 mile running. The La-Ti film is shown by a photograph at ×3000 in FIG. 11. The thickness of this film is 2 μm. This film swelled by the absorption of Ba and Sn from the surrounding $BaSnO_3$ from its original thickness of 1 μm. FIG. 12(A) shows another La-Ti film after 50,000 mile running at a magnification of ×800 and FIG. 12(B)~(D) show the distributions of La, Pt, and Sn at a magnification of ×800, respectively, in the same position. In these experiments $ZrO_2$-added Pt wires were used as the electrodes 8, 10. The solution of Sn into the electrode was prevented almost perfectly by the La-Ti film.

The specimen of FIGS. 12 was examined by local elementary analysis about Ba, Sn, Pt, and La concentrations after the 50,000 mile running. The results of this test are shown in table 2 in atm % unit.

TABLE 2

| Elementary Analysis of La—Ti Film | | | | |
|---|---|---|---|---|
| the measuring point | Ba | Sn | Pt | La |
| inside the electrode | — | — | 100 | — |
| in the La—Ti film | 40 | 40 | 10 | 10 |
| outside the film 1 | 50 | 50 | — | — |
| outside the film 2 | 50 | 50 | — | — |

TABLE 2-continued

| Elementary Analysis of La—Ti Film | | | | |
|---|---|---|---|---|
| the measuring point | Ba | Sn | Pt | La |
| outside the film 3 | 50 | 50 | — | — |

*The spot size of the analysis was 1.5 μm in diameter, the measuring points were positioned on a straight line from the inside to the outside of the electrode.

The main constituents of the La-Ti film were Ba and Sn; the ratios of Ba/La and Sn/La were 4. The Pt in the film arose from the electrode. Even considering the fact that the film swelled to a double thickness by 50,000 mile running, the film had contained Ba and Sn from the first. This means that not a simple La-Ti oxide film but a complex oxide film of La-Ti oxide and $BaSnO_3$ had been formed from the first. The problem that while $La_2Ti_2O_7$ film was insultaing the actually formed film was conductive may be explained by the supposition that the formed film was conductive. The problem that while the film swelled to a double thickness the drift of sensor characteristics was small is also explainable by supposing that the complex oxide film of La-Ti oxide and $BaSnO_3$ had been formed from the first. To the contrary if the initial film had contained La-Ti oxide only, the sensor characteristics should have been greatly changed by the absorption of $BaSnO_3$. The drift of the sensor characteristics is small because both the initial state and the final state of the film have been the complex oxide film of La-Ti oxide and $BaSnO_3$ and the film characteristics have been changed continuously from the initial state to the final state.

What is claimed is:

1. An exhaust gas sensor including a perovskite compound $ASnO_3$ where A represents at least one member selected from the group consisting of Ba, Sr, and Ca, and at least a pair of noble metal electrodes contacted to the $ASnO_3$, the exhaust gas sensor being characterized in that an electrically conductive complex oxide film of $ASnO_3$ and a base metal oxide, whose base metal constituent is different from each metal constituent of $ASnO_3$, is deposited on the surface of the electrodes at the portion thereof in contact with $ASnO_3$.

2. An exhaust gas sensor as defined in claim 1, wherein the base metal oxide is at least one memeber selected from the group consisting of La oxide, oxide of La and a transition metal element, oxide of Fe and Co, oxide of Fe and an alkaline earth metal element which is different from the alkaline earth metal element of $ASnO_3$, and oxide of an alkaline earth metal element which is different from the alkaline earth metal element of $ASnO_3$.

3. An exhaust gas sensor as defined in claim 2, wherein $ASnO_3$ is $BaSnO_3$, and the base metal oxide is at least one member selected from the group consisting of an oxide of La and Ti, an oxide of Sr and Fe, and Mg oxide.

4. An exhaust gas sensor as defined in claim 3, wherein the base metal oxide is an oxide of La and Ti.

* * * * *